United States Patent [19]
Meyer et al.

[11] Patent Number: 6,077,283
[45] Date of Patent: Jun. 20, 2000

[54] DIAMOND SCALPEL FOR OPENING THE MENINX

[75] Inventors: Hans-Jörg Meyer, Ipsach; Frank Ziemer, Port, both of Switzerland

[73] Assignee: Anton Meyer & Co. KG, Nidau, Switzerland

[21] Appl. No.: 09/055,366

[22] Filed: Apr. 6, 1998

[30] Foreign Application Priority Data

Apr. 7, 1997 [EP] European Pat. Off. ............ 97 810 200

[51] Int. Cl.$^7$ .................................................. A61B 17/32
[52] U.S. Cl. ................................................................ 606/167
[58] Field of Search ...................... 606/167, 171, 606/172, 181, 170, 180, 182, 166; 30/353, 356, 357

[56] References Cited

U.S. PATENT DOCUMENTS

| | | | |
|---|---|---|---|
| 1,194,044 | 8/1916 | Loomis | 30/353 |
| 2,049,898 | 8/1936 | Driest | 30/353 |
| 4,499,898 | 2/1985 | Knepshield et al. | 606/167 |
| 4,516,575 | 5/1985 | Gerhard et al. | 606/172 |
| 4,534,348 | 8/1985 | Fedorov et al. | 606/172 |
| 5,254,128 | 10/1993 | Mesa . | |
| 5,376,099 | 12/1994 | Ellis et al. | 606/167 |
| 5,611,805 | 3/1997 | Hall | 606/172 |

FOREIGN PATENT DOCUMENTS

| | | | |
|---|---|---|---|
| 0261242 | 3/1988 | European Pat. Off. . | |
| 195 04 397 | 10/1995 | Germany . | |
| 0671872 | 10/1989 | Switzerland . | |
| 1335263 | 9/1987 | U.S.S.R. . | |
| 1424814 | 9/1988 | U.S.S.R. | 606/167 |
| 923280 | 4/1963 | United Kingdom . | |
| 2113550 | 8/1983 | United Kingdom . | |

*Primary Examiner*—Jeffrey A. Smith
*Assistant Examiner*—Eduardo C. Robert
*Attorney, Agent, or Firm*—Rothwell, Figg, Ernst & Kurz, P.C.

[57] ABSTRACT

A scalpel has a handle, houses a mounting in which a diamond blade is mounted. A foot holder with slotted foot is fastened to the handle a fixed axial distance therefrom. The mounting can be moved axially to a first or second position with the aid of a cylinder so that the tip of the blade projects either 0.3 mm beyond the bottom surface of the foot or is located inside the contour of the foot. With the scalpel the meninx can be opened simply and safely.

9 Claims, 2 Drawing Sheets

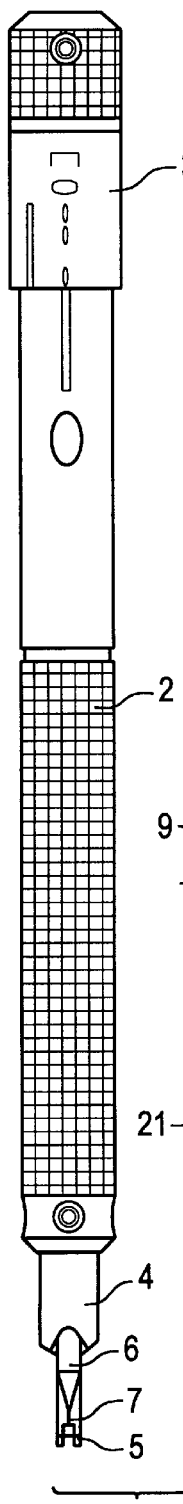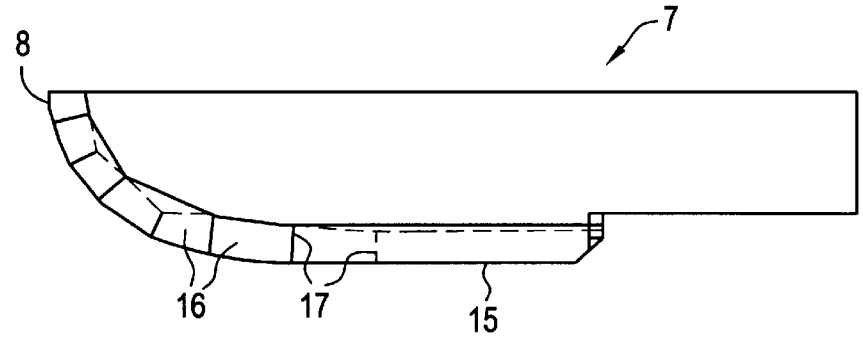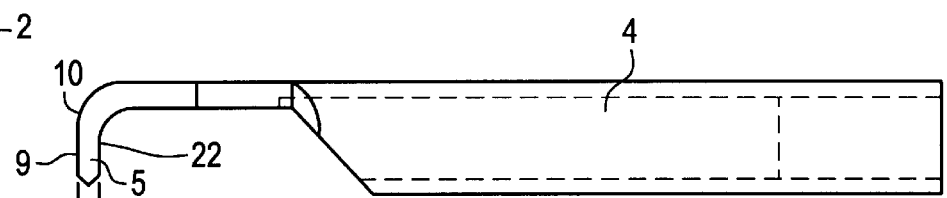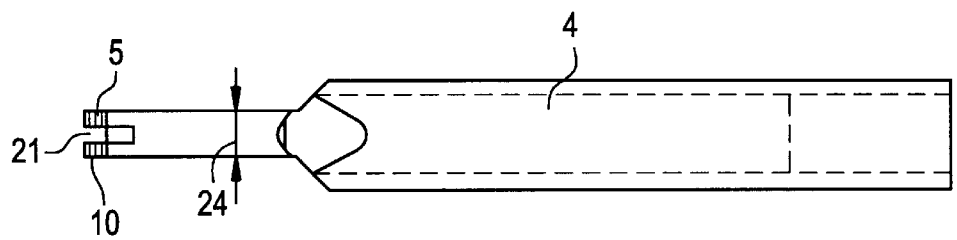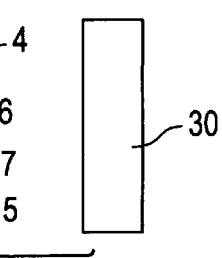

DIAMOND SCALPEL FOR OPENING THE MENINX

BACKGROUND OF THE INVENTION

1. Field of the Invention

The present invention relates to a scalpel for opening the meninx.

2. Description of Related Art

The opening of the meninx is a procedure that has existed since the beginning of neurosurgery. Since the end of the nineteenth century, but primarily after the start of modern neurosurgery, primarily scissors were used for the surgical opening of the meninx. Moreover, fine surgical forceps are also used to pull the unimpaired meninx from the piarachnoid surface. The opening process is done with a knife. Then the meninx is incised with pointed curved scissors. It is often advantageous to put a small moist wad of cotton under the meninx through the first opening in order to protect the cerebral cortex lying underneath. It is also possible to use a small grooved probe and a knife to open the meninx. For repeated openings the knife should be used carefully owing to synechiae between the pachy- and leptomeningeal surfaces or between the meningeal cortex and vessels.

The opening of the meninx can be an easy and safe, but also a very difficult procedure. The difficulties are a function of various factors:

thickness of the meninx additional meningeal sinuses pontine vessels inside the meningeal surface aggressiveness of the swollen and thus weak brain and the virtual subarachnoid space. In such a state the opening of the meninx becomes a difficult and potentially dangerous procedure.

SUMMARY OF THE INVENTION

The present invention is based on the problem of providing an instrument with which the opening of the meninx is simpler and safer. This problem is solved by providing a scalpel capable of allowing reliable use. In accordance with the present invention, a handle having an axis supports further components. A blade having a curved end projects from a handle. A slotted foot also is supported to the handle. The blade has a first axial position inwardly of the blade and a second axial position wherein the tip of the blade projects through a slot in the foot. The foot prevents further progress of the blade in a cutting direction when an impediment is reached. The foot also facilitates placement of the blade when it is desirable to have the scalpel in position on a patient prior to making an incision.

BRIEF DESCRIPTION OF THE DRAWINGS

In the following one embodiment of the invention is explained with reference to the drawings.

FIG. 1 is a view of a scalpel, according to the invention;

FIGS. 2 and 3 are views of the blade;

FIGS. 4 and 5 are views of the foot holder; and

DESCRIPTION OF THE PREFERRED EMBODIMENTS

Figure 6:
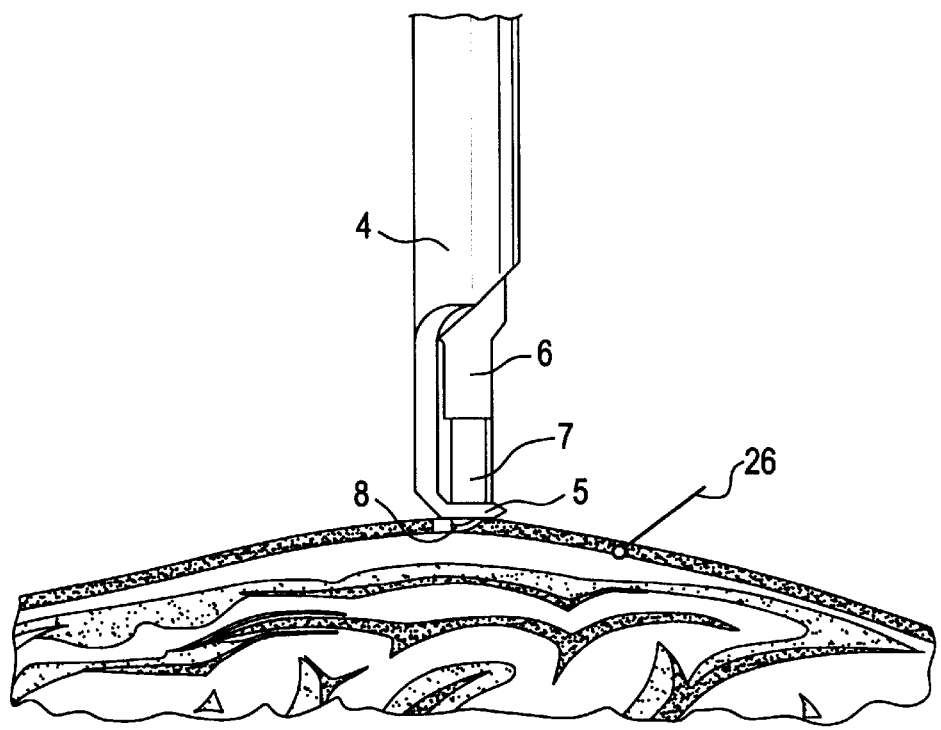
FIGS. 6 and 7 depict the scalpel during the opening process of the meninx.

The scalpel, according to FIG. 1, has a handle 2 with a control cylinder 3. A foot holder 4 with a slotted foot 5 is attached to the handle 2. In the handle 2 a rod-shaped mounting 6 is secured so as to slide longitudinally but not to rotate. In the mounting 6 a diamond blade is fastened. The mounting 6 can be switched, for example, in the manner described in the published swiss specification CH-PS-671 872 between two axial positions by means of the control cylinder 3. U.S. Ser. No. 07/193,067 and Swiss CH-PS-671, 812 disclose a diamond scalpel. A holder, on which the cutting blade in mounted, is longitudinally displaceable in the handle and preloaded rearwards against a front face of a shaft. At its rear end the shaft carries an actuating knob. A cross pin is inserted into the shaft and projects beyond is surface on one side. A sleeve that has six longitudinally slots of different lengths is mounted in the handle. The cross pin abuts the foot of one of the slots. The amount by which the blade tip projects beyond a front face of an L-shaped foot of the handle can be adjusted in steps of 0.1 mm between 0.4 mm and 0.8 mm by choosing the appropriate slot in the sleeve. One of the slots is considerably longer so that, when the cross pin is turned to this slot, the blade is withdrawn completely into the handle. In a second embodiment the switching mechanism is like the switching mechanism of a ball point pen. In the first position the tip 8 of the diamond blade 7 projects 0.3 mm beyond the bottom surface 9 of the foot 5. In the second position the tip 8 is inside a contour 10 (FIGS. 4 and 5) of the foot 5. The contour 10 is a three dimensional outline of the foot 5.

FIGS. 2 and 3 show enlarged views of the blade 7. It is 0.2 mm thick and has a curved cutting edge 15, which is formed by successive, flat facets 16. The edges 17 between the adjacent facets 16 are staggered on both sides of the blade 7. The foot holder 4 with the foot 5 is shown enlarged in FIGS. 4 and 5. The blade 7 projects through the slit 21 of the foot 5. The free end of the foot 5 is chamfered at a 45° angle from the direction of the bottom surface 9 and the top surface 22. The thickness 23 of the foot 5 is 0.6 mm and the width 24 is 1.5 mm.

The scalpel also has a protective sleeve 30 with a graduated passage borehole, which can be snapped onto the front end of the handle 2, envelops the foot holder 4 with play and projects beyond the foot 5.

Figure 7:
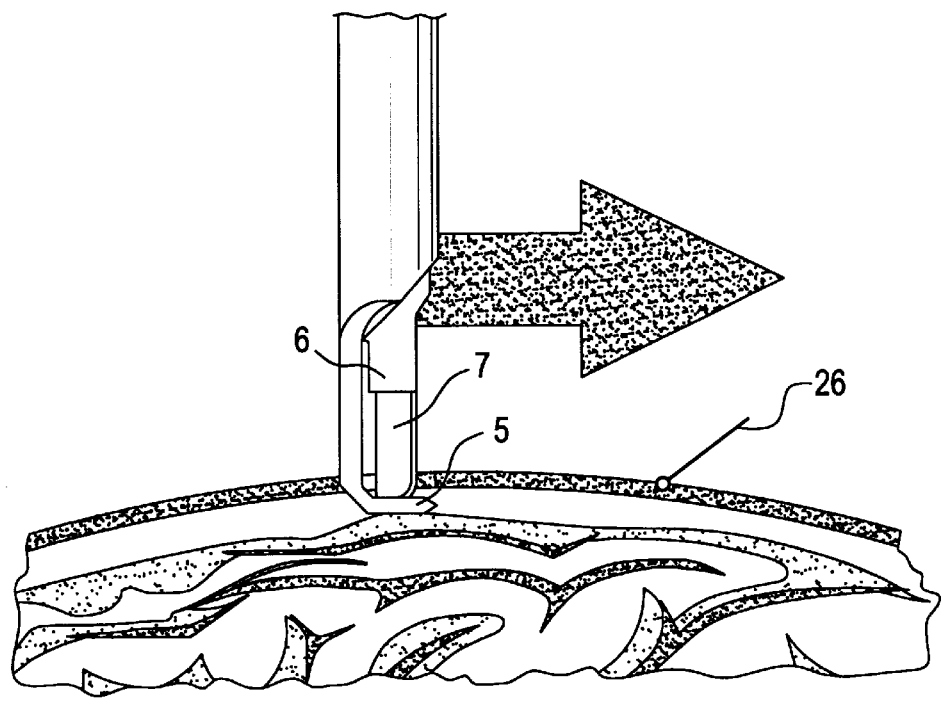

FIG. 6 depicts the front end of the scalpel as the meninx 26 is cut open. The blade 7 is in the first position. The meninx is pulled away by small surgical forceps and incised with the blade to a depth of a few millimeters. Then the blade 7 is retracted into the second position, and the foot 5 is pushed through the initial incision under the meninx 26. With the foot 5 the meninx 26 is now pulled toward the outside, and the blade 7 is pulled in the desired direction. It cuts readily and accurately into the pachymeninges (FIG. 7). The described scalpel is highly useful in the following cases:

opening the meninges of the spinal cord

"key hole" surgery surgery in the posterior fossa surgery in the sitting or semi-sitting position The described scalpel and the described method have several advantages over the state-of-the-art method.

The meninx can be retracted with the foot 5.

The arachnoid cortex of the brain is protected, because the tip 8 of the blade is inside the contour 10 of the foot 5 during the cutting procedure.

The diamond scalpel permits a smooth, fine and precise incision with a blade that never needs sharpening (when handled properly).

The foot of the scalpel guarantees that in the event of an impediment, the progress of the scalpel will be stopped.

Its microscopically small foot continues to move until it reaches an impediment (such as the lateral corner of the SSS). Thus, inadvertent harm (injury) is unlikely. However, should this happen, the tear will be so small that it can be readily closed with a single vascular stitch (7-0).

The curved cutting edge guarantees a more uniform type of incision. Even with slight tilting movements a precise incision is possible.

What is claimed is:

1. A diamond meninx scalpel for opening the meninx, the scalpel comprising:

a handle having an axis and a mounting axially slidably supported in said handle, a blade supported by said mounting adjacent a front end of said handle and having a blade tip and a cutting edge, a slotted foot, which is fastened to the handle and axially displaced therefrom, said foot having a contour comprising a three dimensional outline of said foot, said blade being axially moveable through a slot in said foot, means for switching said mounting exclusively between two positions, wherein said blade tip projects beyond a distal surface of said foot with respect to said handle in a first position by a predetermined amount and is within said contour of said foot in a second position.

2. The scalpel, as claimed in claim 1, wherein a radially extending free edge of said foot is chamfered from the direction of both said distal surface and a proximal surface.

3. The scalpel, as claimed in claim 1, wherein an axial thickness of said foot is about 0.6 mm.

4. The scalpel, as claimed in claim 1, wherein the cutting edge of the blade is ground so as to be curved.

5. The scalpel, as claimed as claim 4, wherein the cutting edge is formed by flat, adjacent facets.

6. The scalpel, as claimed in claim 5, wherein edges between adjacent facets are staggered on one side of the blade with respect to edges of adjacent facets on an opposite side of the blade.

7. The scalpel, as claimed in claim 5, wherein said blade tip projects in the first position at most 0.5 mm beyond said distal surface of said foot.

8. The scalpel, as claimed in claim 5, further comprising a protective sleeve, which is snapped onto a front end of the handle and which projects axially beyond said foot in an attached state.

9. The scalpel, as claimed in claim 5, wherein said blade tip projects in the first position about 0.3 mm beyond said distal surface of said foot.

* * * * *